United States Patent [19]
Clauss, Jr.

[11] Patent Number: 5,584,578
[45] Date of Patent: Dec. 17, 1996

[54] DROP-IN IMMERSION PROBE

[75] Inventor: Harry G. Clauss, Jr., Delanco, N.J.

[73] Assignee: Heraeus Electro-Nite International N.V., Antwerpen, Belgium

[21] Appl. No.: 393,953

[22] Filed: Feb. 24, 1995

[51] Int. Cl.$^6$ .................................................. G01K 1/12
[52] U.S. Cl. ........................... 374/140; 374/208; 136/234
[58] Field of Search ..................................... 374/139, 140, 374/208; 266/80, 88, 99, 225, 78; 136/230, 231, 232, 233, 234, 242

[56] References Cited

U.S. PATENT DOCUMENTS

| | | | |
|---|---|---|---|
| 3,374,122 | 3/1968 | Cole | 136/234 |
| 3,501,957 | 3/1970 | Jones, Jr. | 374/140 |
| 3,756,082 | 9/1973 | Bardenheuer et al. | 136/234 |
| 3,791,209 | 2/1974 | Norburn | 374/140 |
| 4,358,630 | 11/1982 | Falk | 136/234 |
| 4,699,014 | 10/1987 | Boron | 374/140 |
| 4,721,534 | 1/1988 | Phillippi et al. | 136/234 |
| 4,881,824 | 11/1989 | Falk et al. | 374/140 |
| 5,198,749 | 3/1993 | Guthrie et al. | 266/99 |
| 5,275,488 | 1/1994 | Stelts | 374/140 |

Primary Examiner—William A. Cuchlinski, Jr.
Assistant Examiner—Andrew Hirshfeld
Attorney, Agent, or Firm—Panitch Schwarze Jacobs & Nadel, P.C.

[57] ABSTRACT

A drop-in immersion probe for inserting into molten metal includes a generally cylindrical measurement head having an axis and a first axial end which is inwardly tapered toward the axis. The measurement head is made of a combination of materials having a combined density greater than the density of the molten metal. A sensor element extends outwardly from the first axial end of the measurement head proximate the axis and a slag cap covers the first end of the measurement head and the sensor element. A leadwire extends outwardly from the measurement head and has one end electrically connected to the sensor element. A portion of the leadwire extending outwardly from the measurement head is preferably covered by a protective sleeve of heat resistant material. In a preferred embodiment, the slag cap and the measurement head are covered with an ablative material to prevent the adherence of slag. Also in a preferred embodiment, the leadwire and protective sleeve are spirally wound upon a leadwire support tube contacting the second axial end of the measurement head.

19 Claims, 2 Drawing Sheets

DROP-IN IMMERSION PROBE

FIELD OF THE INVENTION

The present invention relates generally to immersion probes for use in measuring parameters of molten metal and, more particularly, to a drop-in immersion probe for the measurement of parameters of molten steel in a basic oxygen furnace.

BACKGROUND OF THE INVENTION

The measurement of the bath temperature of molten metal, such as molten steel, in a basic oxygen furnace is very important to the refining and subsequent processing of the liquid steel produced in the furnace. One well-used method of measuring the molten steel temperature is to temporarily interrupt the refining process, tilt the furnace to a generally horizontal position, and manually insert a consumable probe containing a temperature sensor or other sensors to a particular depth in the liquid steel. While this method has been effective in determining the molten steel temperature and other parameters, it is time consuming and quite disruptive of the steel-making process.

During the mid-1960's, so-called "throw-in" thermocouple sensor devices were introduced to permit the measurement of the temperature of the molten steel while avoiding the costly, time-consuming procedure involved in the tilting and manual measurement process. Typical throw-in sensor devices employed at that time are described in U.S. Pat. Nos. 3,374,122 and 3,497,398. The sensor devices shown in these patents employ a standard or typical thermocouple-type sensor attached to a paper or cardboard support tube and a separate weight element which surrounds at least a portion of the support tube for the purpose of causing the sensor device to sink into the molten steel. The furnace would remain in an upright position and the sensor device would be dropped approximately 60 to 70 feet into the molten steel in the furnace. A leadwire of a suitable length connected the thermocouple sensor to instrumentation located outside of the furnace for interpreting the sensed temperature of the molten steel. Such sensor devices were deficient due to their tendency to float at the slag/metal interface which often resulted in inaccurate temperature measurements. The flotation problem was primarily a result of the sensor devices having a net density which, despite the additional weight element, was less than the density of the liquid steel. Such sensors also had a high center of gravity which resulted in inaccurate measurements.

An alternate method of making temperature measurements in a basic oxygen furnace employed a motorized lance or probe with multi-purpose temperature and/or other sensors which also did not require the tilting of the furnace or the interruption of the refining process. Such motorized systems, while providing generally good temperature measurement results, required multi-million dollar expenditures for system installation and were also demonstrated to be costly to operate and maintain.

More recent developments in basic oxygen furnace throw-in sensor devices are disclosed in U.S. Pat. Nos. 4,881,824 and 5,275,488. U.S. Pat. No. 4,881,824 discloses an immersible probe having a counter-weight and float which is employed to maintain a temperature sensor at a prescribed depth for the proper measurement of the molten steel temperature. The described probe has a net density which is less than that of liquid steel and has a high center of gravity, resulting in the probe maintaining a generally vertical orientation in the molten steel only as long as the slag layer above the steel is of a sufficient minimum thickness. U.S. Pat. No. 5,275,488 discloses a probe having a net density which is greater than the density of the molten steel. However, this patent does not address additional factors such as entrapped gas buoyancy and high center of gravity, both of which detrimentally affect the effectiveness of the temperature measurement.

A probe having a density greater than that of molten steel will not necessarily sink into the molten steel, specifically a high oxygen, low carbon steel typically present in a basic oxygen furnace. Gas evolution from the carbon-oxygen reaction at the surface of such a probe results when the relatively cold sensor head of the probe contacts the highly oxygenated steel in the steel bath. The gas evolution at the sensor head/liquid steel interface results in a flotation force being applied to the sensor head which pushes the probe upwardly away from the area at which the temperature measurement should be made. The probes disclosed in both patents include a rigid metallic tube over the leadwire at the sensor head end to prolong the life of the leadwire in the molten steel bath. Although protecting the leadwire from the molten metal, the rigid metallic tube creates a higher center of gravity for the probe which results in vertical instability of the probe when immersed in the liquid steel. The shape of both of the probe sensor heads is not particularly conducive to deep probe penetration into the molten metal. In addition, the use of metal support legs, as shown in U.S. Pat. No. 4,881,824 in the vicinity of the sensor element results in temperature measurement errors due to thermal gradients produced by liquid steel solidification on the support legs as well as the previously described gas evolution which occurs during the initial cold probe immersion into the molten steel bath.

Based upon the foregoing, it has been determined that the forces tending to minimize penetration of the sensor head of a probe into the molten steel are those resulting from viscous drag of the gas atmosphere within the furnace, slag and liquid steel, the retarding force of the trailing probe leadwire, the net density of the probe as compared to the density of the liquid steel, the effective density decrease as a result of slag adhering to the sensor during insertion into the molten steel, and gas evolution at the sensor head due to metal solidification. The molten steel circulation in the furnace also aids or retards sensor head penetration into the molten steel. If all of these factors result in a net downward force, the sensor head continues to sink until the sensor leadwire is taut or the probe contacts the bottom of the furnace. If these forces result in a net upward force, the probe rises to the slag metal interface or into the slag.

The present invention comprises a drop-in consumable immersion probe designed to economically increase probe penetration into the liquid steel while minimizing retarding and buoyancy forces. The penetration force of the present probe is increased by increasing the effective probe density using steel for the sensor head and minimizing internal cavities by using a miniature thermocouple element and filling all remaining voids in the sensor head with a dense particulate material. The retarding forces are further minimized by providing the probe with a projectile-like shape which is conducive to deep penetration of the probe into the molten steel. The projectile-like shape minimizes gas entrapment as well as slag and molten steel drag on the probe during immersion. The slag cap of the present probe as well as the steel measurement head are preferably provided with an ablative coating to further retard slag adherence. The conical shape of the probe measurement head also minimizes thermal gradients in the area of the temperature sensing element resulting in a more representative temperature measurement of the molten steel. Finally, a heat resistant oversleeve is provided around at least the portion of the sensor leadwire exposed to the molten steel for extending the life of the leadwire when the probe is immersed into the molten steel.

SUMMARY OF THE INVENTION

Briefly stated, the present invention comprises a drop-in immersion probe for inserting into molten metal. The probe includes a generally cylindrical measuring head having an axis and a first axial end which is inwardly tapered toward the axis. The measurement head is made of a combination of materials having a combined density greater than the density of the molten metal. A sensor element extends outwardly from the first end of the measurement head proximate the axis. A slag cap is employed for covering the first end of the measurement head and the sensor element. A leadwire extends outwardly from the measurement head, the leadwire having one end electrically connected to the sensor element. A portion of the leadwire extending outwardly from the measurement head is covered by a protective sleeve of heat resistant material. In the preferred embodiment, the measurement head is made of steel and both the slag cap and measurement head are covered with an ablative material that prevents slag from adhering. In addition, in the preferred embodiment, all internal cavities of the measurement head are filled with a particulate material and a support tube contacting the second axial end of the measurement head is provided for supporting the leadwire.

BRIEF DESCRIPTION OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred, it being understood, however, that the invention is not limited to the specific methods and instrumentalities disclosed. In the drawings.

DESCRIPTION OF PREFERRED EMBODIMENT

Figure 1:
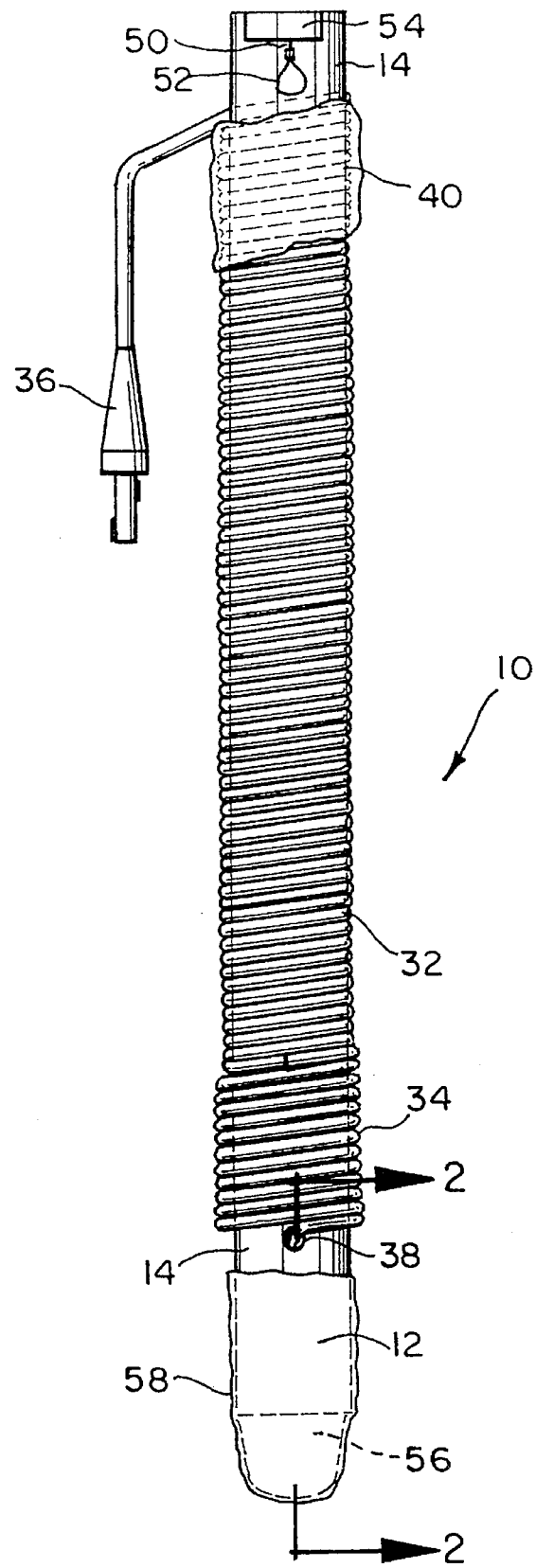
FIG. 1 is an elevational view of a preferred embodiment of a drop-in immersion probe in accordance with the present invention.

Referring to the drawings, wherein like numerals are used to indicate like elements, there is shown in FIG. 1 a preferred embodiment of a drop-in immersion probe 10 in accordance with the present invention. The drop-in immersion probe 10 is of the type which is preferably employed for the purpose of measuring one or more parameters of the molten steel being refined in a basic oxygen furnace (BOF). More particularly, the present embodiment of the probe 10 is employed for measuring the temperature of the molten steel in such a molten steel bath. It will, of course, be appreciated by those skilled in the art that the present invention is not limited to a probe which is employed only for making temperature measurements nor is it limited to a probe for use in measuring molten steel or even molten steel in a BOF. Thus, it should be clearly understood that a probe in accordance with the present invention could be employed for measuring other parameters of a molten metal, other than steel, in virtually any type of molten metal processing.

Figure 2:
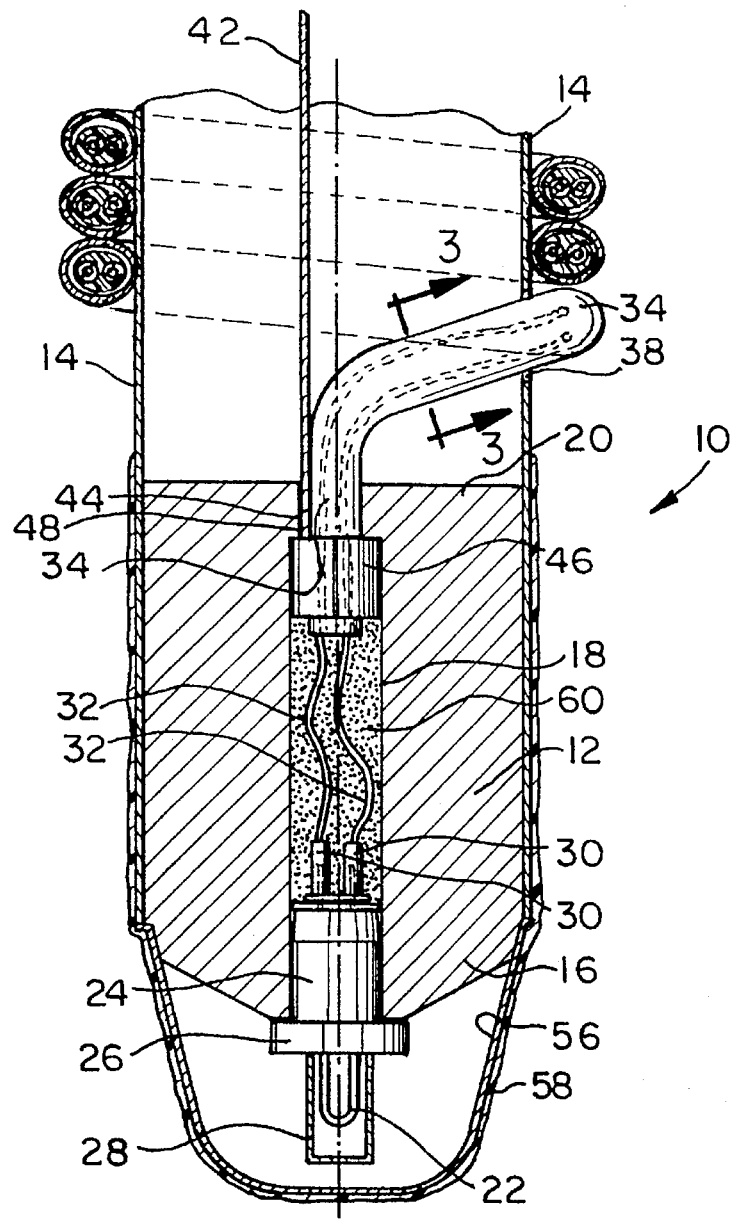
FIG. 2 is an enlarged sectional view of a portion of the probe of FIG. 1 taken along line 2—2.
Figure 3:
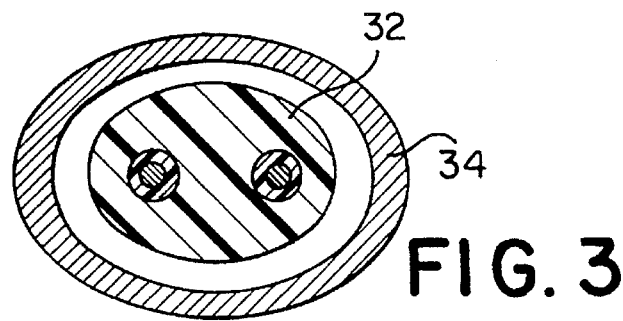
FIG. 3 is an enlarged sectional view taken along line 3—3 on FIG. 2.

In the present embodiment, the drop-in immersion probe 10 is comprised of two principal assemblies, a measurement head 12 and an elongated, generally cylindrical leadwire support tube 14, a portion of which surrounds the measurement head 12. As best shown in FIG. 2, the measurement head 12 is generally cylindrically shaped, is generally symmetrical about its vertical axis, and includes a first axial end 16 which is generally inwardly tapered toward the axis so that the first axial end 16 is generally conically shaped. Preferably, the measurement head 12 is made of materials having a combined net density which is greater than the density of the molten metal within which the probe 10 is to be inserted. Typically, molten steel produced in a BOF has a density of approximately 7.0 grams per cubic centimeter. The present embodiment of the measurement head 12 also has a density greater than 7.0 grams per cubic centimeter. It will, of course, be appreciated that the density of the measurement head 12 will vary depending upon the particular molten metal being measured, the particular process being employed, as well as other parameters of the molten metal.

In the presently preferred embodiment, the measurement head 12 is formed primarily of steel and, preferably, dense steel bar stock rather than cast steel. The sensor head 12 further includes a generally cylindrical bore 18 extending generally through the axial center of the measurement head 12 from the first axial end 16 to the second axial end 20. A sensor element, in the present embodiment, a platinum alloy thermocouple having Type B calibration of a type typically employed in the steel making art is encased within a generally U-shaped quartz tube 22, the ends of which are secured by refractory cement or any other suitable refractory material in a ceramic housing 24. In the present embodiment, the ceramic housing 24 is generally cylindrically shaped and is sized to snugly fit within the bore 18 of the measurement head 12. An annular flange 26 having a diameter which is at least slightly greater than the diameter of the remainder of the ceramic housing 24 abuts against the first axial end 16 of the measurement head 12 for correct positioning of the quartz tube 22. The ceramic housing 24 may be secured within the axial bore 18 using a refractory cement or other suitable material. A thimble-shaped thin metal shield 28 initially surrounds and generally encloses the U-shaped quartz tube 22. The shield 28 protects the fragile quartz tube 22 and the encased thermocouple during initial insertion of the probe 10 into the molten metal bath until the shield 28 melts after it contacts the liquid steel for a predetermined time period.

The opposite axial end of the ceramic housing 24 includes a pair of metallic contacts 30 which are electrically connected to the thermocouple within the U-shaped quartz tube 22. Two conductor leadwire, typically 18 AWG, 2 conductor rubber insulated and jacketed cable 32 is secured to the contacts 30 and extends through the bore 18 and out of the second axial end 20 of the measurement head 12. The distal end of the leadwire 32 is terminated in a standard electrical connector member 36 such as a modified Electro-Nite EN-3 contact assembly or any other type generally well known and commercially available for use in coupling the sensor output to standard or typical instrumentation (not shown) for obtaining and processing the temperature measurements obtained by the thermocouple.

The lifetime of the leadwire 32 is approximately six to eight seconds in liquid steel. The lifetime may be extended by use of a protective sleeve 34 positioned over at least the portion of the leadwire 32 which is exposed to the liquid steel. The protective sleeve 34, which preferably is made of a rubber-like compound, provides thermal insulation for the exposed portion of the leadwire 32 when the probe 10 is immersed into the molten steel. The protective sleeve 34 extends beyond the measurement head 12 by a predetermined length selected for at least the maximum anticipated depth of immersion of the probe 10 into the liquid steel. In the presently preferred embodiment, the portion of the protective sleeve 34 extending beyond the measurement head 12 is approximately six feet. However, the protective sleeve 34 could be longer or shorter for a particular application depending upon the depth within the molten steel that the sensor 10 is to be immersed. In this manner, the protective sleeve 34 extends the lifetime of the leadwire 32 correspondingly extending the length of time the temperature measurements may be taken in the liquid steel. The lifetime of the leadwire 32 with the protective sleeve 34 is extended to approximately sixteen seconds. Preferably, as best shown in FIG. 1, the protective sleeve 34 and the encased leadwire 32 are spirally wound around the leadwire support tube 14. Alternatively, the protective sleeve 34 and leadwire 32 may be wound or folded inside of the support tube 14. An opening or slot 38 is provided in the support tube 14 for passage of the protective sleeve 34 and leadwire 32 to the outer surface of the support tube 14. Preferably, a portion of the leadwire 32 is weakly attached to the distal end of the support tube 14 using a commercially available stretch wrap material 40 which extends over a small portion of the spirally wound leadwire 32. The strength of the wrap material 40 is sufficient to maintain the leadwire 32 on the support tube 14 during manufacturing, shipping and handling of the probe 10 but is sufficiently weak to permit the leadwire 32 to uncoil and easily separate from the support tube 14 when the probe 10 is employed for taking a temperature measurement in a manner which will hereinafter be described.

A separate elongated support member is provided for supporting the probe 10 prior to insertion of the probe 10 into the molten steel. In the presently preferred embodiment, the support member comprises a steel support cable 42 having a first end 44 which is secured proximate the second axial end 20 of the measurement head 12. In the present embodiment, the first end 44 of the support cable 42 and the leadwire 32 are secured within the bore 18 of the measurement head 12 using a commercially available dog-eared cable grip member 46 having an outer diameter which is substantially the same as the inner diameter of the bore 18. The cable grip member 46 engages an inwardly extending annular shoulder 48 proximate the second axial end 20 of the measurement head 12. A potting compound, for example, a resin set epoxy, refractory sealing cement, or other suitable material (not shown) may be employed for securing the cable grip member 46, the first end 44 of the support cable 42 and the leadwire 32 to the measurement head 12. The second end 50 of the steel support cable 42 is formed into a generally circular loop 52. The loop 52 may thus be attached to a hook or other member for supporting the probe 10 over a molten steel bath prior to immersion of the probe 10. Preferably, the steel support cable 42 is at least slightly longer than the overall length of the support tube 14 so that at least a portion of the support cable 42 extends beyond the distal end of the support tube 14. To facilitate handling of the probe 10 during transport, the second end 50 of the support cable 42 is attached to the distal end of the support tube 14 by a strip of tape 54 or in any other suitable manner. The probe 10 may be removed from its shipping carton either by grasping the support tube 14 or the loop 52 of the support cable 42.

A slag cap 56 covers the first end 16 of the measurement head. The slag cap 56 which is made of steel having a thickness of 0.030 inches is generally frustaconically shaped and is employed for covering and protecting the U-shaped quartz tube 22 containing the thermocouple as the probe 10 passes through a slag layer when it is immersed into molten steel. As best shown in FIG. 1, the shape of the slag cap 56 in combination with the measurement head 12 and support tube 14 gives the probe 10 a projectile-like appearance. In the presently preferred embodiment, the outer surface of the slag cap 56 is covered with a material layer 58 that retards or prevents slag from adhering to the slag cap 56 as the probe 10 passes through the slag layer. In the present embodiment, the material layer 58 is formed of an ablative material although it will be appreciated by those skilled in the art that other materials may alternatively be employed. As best shown in FIG. 2, the ablative material layer 58 also covers the outer surface of the measurement head 12. The ablative material layer 58 in the present embodiment is comprised of an organic compound that decomposes when contacted with high temperature slag, forming a gas layer that prevents or retards slag from adhering to the slag cap 56. The slag cap 56, in addition to protecting the measurement head 12 from damage as the probe impacts with the slag, prevents slag from adhering to the shield 28 or to the U-shaped quartz tube 22 housing the thermocouple. The slag cap 56 may also have an opening in the axial end to facilitate rapid melting of the slag cap 56 in liquid steel.

The internal cavity formed by the portion of the bore 18 between the ceramic housing 24 and the cable grip member 46 as well as any other voids (not shown) within the measurement head 12 are filled with a particulate material 60 to increase the effective density of the measurement head 12. In the present embodiment, the particulate material 60 is a very dense material such as zircon sand. However, the particulate material 60 could be a dense metallic material, if desired, or some other type of particulate material. Particulate material is preferred over a solid castable material because the use of particulate material reduces the stresses on the sensor components when the probe 10 is immersed into the molten steel and allows for limited movement of the leadwire 32 between the ceramic housing 24 and the cable grip member 46.

In using the probe 10 for measuring the temperature of steel within a molten steel bath, a suitable drop mechanism is employed to grasp the loop 52 on the distal end of the steel support cable 42 and the connector member 36 is plugged into a suitable complementary connector member (not shown) associated with instrumentation located outside of the molten metal bath. The probe 10 is lifted by the drop mechanism to a suitable height above the molten steel bath in a generally vertical orientation with the measurement head 12 and slag cap 56 pointing downwardly. Typically, the probe 10 is raised to a height of approximately fifty to seventy feet above the molten steel. The probe 10 is thereafter released by the drop mechanism to move downwardly into the molten steel. As the probe 10 descends toward the surface of the molten steel, the protective sleeve 34 and leadwire 32 are unravelled from the support tube 14. The potential energy and projectile-like shape of the probe 10 combined with the high net density of the measurement head 12 and the ablative material layer 58 on the slag cap 56 and measurement head 12 result in adequate penetration of the probe 10 through the slag layer and into the molten steel at an appropriate depth for taking the temperature measurement. The combination of the high density measurement head 12 and the low center of gravity of the probe 10 helps to maintain vertical stability of the probe 10 as it passes through the slag layer and into the molten steel. The conical shape of the slag cap 56 in combination with the ablative material layer 58 of the slag cap 56 and the outer surface of the measurement head 12 assists in moving the probe 10 quickly through the slag layer and prevents or minimizes buildup of slag on the slag cap 56 or measurement head 12 which could provide drag which would slow the downward movement of the probe 10 and which could also decrease the net density of the probe 10. Once the slag cap 56 is dissolved, the generally conical shape of the first axial end 16 of the measurement head 12 minimizes entrapped gas to reduce buoyant forces on the probe 10 and to minimize thermal gradients in the area of the U-shaped quartz tube 22 which contains the thermocouple thereby providing a more accurate temperature measurement of the molten steel. The protective sleeve 34 protects the leadwire 32 from the detrimental effects of the molten steel for a substantial period of time permitting enhanced 35 measurement of the molten steel.

From the foregoing description of a preferred embodiment, it can be seen that the present invention comprises a drop-in immersion probe for inserting into molten metal for measuring one or more parameters of the molten metal. It will be appreciated by those skilled in the art that changes or modifications could be made to the above-described embodiment without departing from the broad inventive concepts of the invention. It should be appreciated, therefore, that the present invention is not limited to the particular embodiment disclosed but is intended to cover all embodiments within the scope or spirit of the appended claims.

I claim:

1. A drop-in immersion probe for inserting into molten metal, the probe comprising:

a generally cylindrical measurement head having an axis, a first axial end which is inwardly tapered toward the axis, and a second axial end;

a sensor element extending outwardly from the first end of the head generally along the axis;

a slag cap substantially completely covering and enclosing the entire first end of the head and the entire sensor element, the slag cap having a first end engaging the measurement head proximate the first axial end thereof and a second end extending axially beyond the sensor element, the slag cap being smoothly inwardly tapered toward the measurement head axis so that the second end of the slag cap has a radial dimension which is less than a radial dimension of the first end of the slag cap so that the slag cap is generally projectile shaped; and a leadwire extending outwardly from the head and having one end electrically connected to the sensor element.

2. The probe as recited in claim 1 wherein the sensor element is a temperature measuring sensor.

3. The probe as recited in claim 1 wherein the sensor element is a temperature measuring and oxygen activity sensor.

4. The probe as recited in claim 1 wherein the slag cap has an outer surface covered with a material that prevents slag from adhering to the slag cap.

5. The probe as recited in claim 4 wherein the material covering the slag cap comprises an ablative material.

6. The probe as recited in claim 5 wherein the at least a portion of the head is covered with an ablative material.

7. The probe as recited in claim 1 wherein the leadwire extends outwardly from the second axial end of the measurement head.

8. The probe as recited in claim 1 further comprising a leadwire support tube contacting the second axial end of the measurement head wherein the portion of the leadwire extending outwardly from the head is spirally wound on the support tube.

9. The probe as recited in claim 1 wherein the leadwire includes another end electrically connected to a connector member.

10. The probe as recited in claim 1 wherein a portion of the leadwire extending outwardly from the head is covered by a protective sleeve of heat resistant material.

11. The probe as recited in claim 1 further including an elongated support member extending outwardly from the measurement head for supporting the measurement head prior to the measurement head being inserted into the molten metal.

12. The probe as recited in claim 11 wherein the support member comprises a cable having a predetermined length and having a first end secured to the measurement head and a second end including a support loop.

13. The probe as recited in claim 12 further comprising a leadwire support tube contacting the second axial end of the measurement head wherein the portion of the leadwire extending outwardly from the head is spirally wound on the support tube and wherein the length of the support cable is such that the second end of the support cable extends beyond the support tube.

14. A drop-in immersion probe for inserting into molten metal, the probe comprising:

a generally cylindrical measurement head having an axis, a first axial end which is inwardly tapered toward the axis, and a second axial end;

a sensor element extending outwardly from the first end of the head generally along the axis;

a slag cap substantially completely covering and enclosing the entire first end of the head and substantially the entire sensor element, the slag cap having an outer surface at least partially covered with an ablative material that prevents slag from adhering to the slag cap; and a leadwire extending outwardly from the head and having one end electrically connected to the sensor element.

15. A combination molten metal bath and drop-in immersion probe for inserting into the molten metal of the bath, the molten metal having a density which is predetermined by the type of molten metal in the bath, the probe comprising:

a generally cylindrical measurement head having an axis, a first axial end which is inwardly tapered toward the axis and a second axial end, the head being made of a combination of materials having an aggregate density greater than the predetermined density of the molten metal of the molten metal bath;

a sensor element extending outwardly from the first end of the head generally along the axis;

a slag cap substantially completely covering and enclosing the entire first end of the head and substantially the entire sensor element, the slag cap being generally smoothly inwardly tapered toward the axis so that the measurement head and the slag cap together are generally projectile-shaped; and a lead wire extending outwardly from the head and having one end electrically connected to the sensor element.

16. The probe as recited in claim 15 wherein the aggregate density of the measurement head is greater than 7.0 grams per cubic centimeter.

17. The probe as recited in claim 16 wherein the measurement head is constructed primarily of steel.

18. The probe is recited in claim 17 wherein the steel is a bar stock.

19. The probe as recited in claim 15 wherein internal cavities within the measurement head are filled with a particulate material to increase the effective density of the head.

* * * * *